United States Patent [19]

Jackson et al.

[11] Patent Number: 5,594,159

[45] Date of Patent: Jan. 14, 1997

[54] PRODUCING CF$_3$CH$_2$CF$_3$ AND/OR CF$_3$CH=CF$_2$ BY THE CONVERSION OF ALPHA-HYDROPERFLUOROISOBUTYRIC ACID COMPOUNDS

[75] Inventors: Scott C. Jackson, Kennett Square, Pa.; Paul R. Resnick; Steven H. Swearingen, both of Wilmington, Del.

[73] Assignee: E I Du Pont De Nemours and Company, Wilmington, Del.

[21] Appl. No.: 421,095

[22] Filed: Apr. 13, 1995

[51] Int. Cl.$^6$ .................. C07C 17/363; C07C 17/361; C07C 19/08; C07C 21/18
[52] U.S. Cl. .......................................... 570/142; 570/159
[58] Field of Search ................................ 570/142

[56] References Cited

U.S. PATENT DOCUMENTS

| | | | |
|---|---|---|---|
| 2,601,536 | 6/1952 | La Zerte | 570/142 |
| 2,668,864 | 2/1954 | Hals et al. | 570/142 |
| 2,746,997 | 5/1956 | Reid et al. | 570/142 |
| 5,329,054 | 7/1994 | Theriot et al. | 570/142 |
| 5,420,368 | 5/1995 | Jackson et al. | 570/142 |

FOREIGN PATENT DOCUMENTS 0002098  5/1979  European Pat. Off. .

OTHER PUBLICATIONS

Koshar, R. J. et al, "The Addition of Alcohols to Octafluoroisobutene", *The Addition of Alcohols to Octafluoroisobutene*, 79, 1741–1744 (1957).

Hall, C. Richard et al, "Protection provided by activated carbon vapour filters against perfluoroisobutene", *Chem. Ind.* (London), 5, 145–156 (1989).

Kocharyan, S. T. et al, "Alkylating Properties of Alkyl Perfluoroisobutenyl Ethers: Communication 1. Complexes of Alkyl Perfluoroisobutenyl Ethers with Trialkylamines", translated from *Izvestiya Akademii Nauk SSSR, Seriya Khimicheskaya*, 4, 846–854, Apr. 1968.

Aktaev, N. P. et al, "Comparison of the Electronic Effects of the Nitrile and Trifluoromethyl Groups", translated from *Izventiya Akademiya Nauk SSSR, Seriya Khimicheskaya*, 5, 1112–1117, May 1977.

Cheburkov, Yu. A. et al, "Bistrifluoromethylketene and Perfluoromethacrylic Acid: Communication 4. Pyrolysis of some Derivatives of α–Hydrohexafluoroisobutyric Acid", translated from *Izvestiya Akademii Nauk SSSR, Seriya Khimicheskaya*, 9, 1573–1576, Sep. 1963.

Chemical Abstracts, 109:189842 (1988) re JP–63–035539.

*Primary Examiner*—Joseph E. Evans

[57] ABSTRACT

A process is disclosed for producing 1,1,1,3,3,3-hexafluoropropane and/or 1,1,1,3,3-pentafluoropropene from (CF$_3$)$_2$CHCOOH and/or its water soluble salts. The process involves providing a mixture containing water and such carboxy compound(s) which has a pH of less than about 4, and reacting the mixture at a temperature of at least about 75° C. Certain ether compounds may be included in the mixture along with (CF$_3$)2 CHCOOH and/or its water soluble salts. The reaction of the carboxy (and optionally ether) compound(s) with water may be employed in connection with a process for producing tetrafluoroethylene and/or hexafluoropropylene by pyrolysis, where by-product perfluoroisobutylene is reacted with water (and optionally an alkanol) to produce (CF$_3$)$_2$CHCOOH (and optionally one or more ether compounds).

12 Claims, No Drawings and/or HFC-1225zc. Accordingly, HFC-236fa and/or HFC-1225zc are produced in accordance with this invention by the reaction of water and at least one carboxy compound selected from $(CF_3)_2CHCOOH$ and its water soluble salts, or by the reaction of water and a combination of said carboxy compound(s) and one or more compounds of the formula $(CF_3)_2CHCF_2OR$ (i.e., the alkylfluorobutyl ether reactants of this invention) and/or $(CF_3)_2C=CFOR$ (i.e., the alkylfluorobutenyl ether reactants of this invention) wherein R is a $C_1$ to $C_6$ alkyl group as defined above (e.g., a mixture comprising the carboxy reactants, the alkylfluorobutyl ether reactants and the alkylfluorobutenyl ether reactants of this invention).

PRODUCING $CF_3CH_2CF_3$ AND/OR $CF_3CH=CF_2$ BY THE CONVERSION OF ALPHA-HYDROPERFLUOROISOBUTYRIC ACID COMPOUNDS

FIELD OF THE INVENTION

This invention relates to processes for the manufacture of hydrofluorocarbons (i.e., HFCs) and more particularly to processes for the production of 1,1,1,3,3,3-hexafluoropropane and/or 1,1,1,3,3-pentafluoropropene.

BACKGROUND

Tetrafluoroethylene and hexafluoropropylene are commonly manufactured by high temperature pyrolysis. In these manufacturing processes, minor amounts of highly toxic perfluoroisobutylene are typically produced. This material can be reacted either with water (optionally in the presence of inert solvents for perfluoroisobutylene such as acetone or tetrahydrofuran) to form $(CF_3)_2CHCOOH$ or with alkanols to form ethers. For example, perfluoroisobutylene may be reacted with methanol to convert it to two less toxic ether compounds, $(CF_3)_2CHCF_2OCH_3$ (herein designated "ether A") and $(CF_3)_2C=CFOCH_3$ (herein designated "ether B") (see, e.g., European Patent Publication No. 0 002 098). While $(CF_3)_2CHCOOH$, ether A and ether B are less hazardous than the perfluoro compound from which they are prepared, they still are generally disposed of as waste product. There is interest in developing means for productive use of $(CF_3)_2CHCOOH$ and ether materials such as ether A and ether B.

SUMMARY OF THE INVENTION

A process is provided in accordance with this invention for producing 1,1,1,3,3,3-hexafluoropropane and/or 1,1,1,3,3-pentafluoropropene from at least one carboxy compound selected from $(CF_3)_2CHCOOH$ and its water soluble salts (and optionally ether A, ether B, and/or certain of their alkyl analogs). The process comprises (1) providing a mixture comprising said at least one carboxy compound (and optionally said ether compound(s)) and water, said mixture having a pH of less than about 4, and (2) reacting the mixture provided in (1) at an elevated temperature of at least about 75° C. The reaction of the mixture of said compound(s) and water may be employed in connection with a process for producing tetrafluoroethylene and/or hexafluoropropylene by pyrolysis, where by-product perfluoroisobutylene is reacted with water to produce α-hydroperfluoroisobutyric acid (and optionally an alkanol to produce the ether compound (s)).

DETAILED DESCRIPTION OF THE INVENTION

The present invention involves the discovery that $(CF_3)_2CHCOOH$ and its water soluble salts can be effectively reacted with $H_2O$ at acidic pH (i.e., pH less than about 4) to provide 1,1,1,3,3,3-hexafluoropropane (i.e., $CF_3CH_2CF_3$ or HFC-236fa) and/or 1,1,1,3,3-pentafluoropropene (i.e., $CF_3CH=CF_2$ or HFC-1225zc). It has also been found that combinations of $(CF_3)_2CHCOOH$ (and/or its water soluble salts) and ether compounds of the formula $(CF_3)_2CHCF_2OR$ and of the formula $(CF_3)_2C=CFOR$ where R is an alkyl group of the formula $C_nH_{2n+1}$ and n is an integer from 1 to 6 (e.g., $CH_3$) can be effectively reacted with water at acidic pH to provide HFC-236fa and/or $(CF_3)_2CHCF_2OR$ and $(CF_3)_2C=CFOR$ can be produced by reacting perfluoroisobutylene with alkanols. A typical procedure for the production of alkylfluorobutyl ethers and alkylfluorobutenyl ethers is disclosed by R. J. Koshar et al., J. Am. Chem. Soc., 79, 1741–44 (1957). The methyl ethers, $(CF_3)_2CHCF_2OCH_3$ (i.e., ether A) and $(CF_3)_2C=CFOCH_3$ (i.e., ether B), are preferred for use in this invention. These may be prepared by using methanol as the alkanol.

As noted above, $(CF_3)_2CHCOOH$ can be produced by reacting perfluoroisobutylene with water. $(CF_3)_2CHCOOH$ can also be produced by treating heptafluoroisobutenyl alkyl ethers with aqueous acids (see Chem. Abstracts 109:1892 (1988)).

Inasmuch as perfluoroisobutylene is produced as a by-product (typically in small amounts) during the production of at least one of tetrafluoroethylene and hexafluoropropylene by pyrolysis (e.g., pyrolysis of chlorodifluoromethane) the present invention provides a convenient method of utilizing the by-product perfluoroisobutylene produced in a process for producing tetrafluoroethylene, hexafluoropropylene, or both tetrafluoroethylene and hexafluoropropylene by that pyrolysis, by reacting the perfluoroisobutylene with water to produce $(CF_3)_2CHCOOH$, and then providing a mixture comprising said $(CF_3)_2CHCOOH$ and water wherein the pH is less than about 4, and reacting said mixture as indicated herein to produce HFC-236fa and/or HFC-1225zc. Also, in accordance with this invention the perfluoroisobutylene can be reacted with a mixture of water and an alkanol of the formula ROH (where R is a $C_1$ to $C_6$ alkyl group as defined above) to produce $(CF_3)_2CHCOOH$ together with $(CF_3)_2CHCF_2OR$ and/or $(CF_3)_2C=CFOR$; and then a mixture comprising water and this combination of $(CF_3)_2CHCOOH$ and ether compounds having a pH of less than about 4 can be provided, and this mixture can be reacted as indicated herein to produce HFC-236fa and/or HFC-1225zc. Of note are embodiments where perfluoroisobutylene is reacted with a mixture of water and methanol.

The carboxy compounds (and optionally $(CF_3)_2CHCF_2OR$ and $(CF_3)_2C=CFOR$, and particularly, ethers A and B) may be reacted with water itself. Optionally acids (e.g., sulfuric acid, hydrochloric acid, acetic acid) may be present. Bases (e.g., sodium hydroxide, sodium bicarbonate, dimethylamine) may also be present provided that the pH is less than about 4. The reaction may also be done in the presence of inert organic materials such as toluene, tetrahydrofuran, acetone, mono- and dialkyl ethers of ethylene glycol where the alkyl group is methyl or ethyl, ethylene glycol, propylene glycol, and methyl ethyl ketone. Inert solvents used to dissolve perfluoroisobutylene and help insure that the perfluoroisobutylene reacts with water and/or alkanols, may be present.

The molar ratio of water to the total amount of carboxy and ether reactant is normally about 1:1 or more, typically ranges from about 1:1 to about 100:1, and is preferably within the range of about 5:1 to about 75:1. The process of the present invention is suitably conducted at a temperature in the range of from about 75° C. to 500° C., and is preferably from about 150° C. to about 250° C. for liquid phase reactions, and from about 150° C. to 400° C. for vapor phase reactions. The reaction time is normally about 0.1 minute, or more, and typically ranges from about 0.1 minutes to about 24 hours. Preferably the pH is about 3 or less; more preferably about 2 or less.

The reaction of the carboxy reactants of this invention (and the alkylfluorobutyl ether reactants and/or the alkylfluorobutenyl ether reactants of this invention, if present) with water may be conducted in either the liquid or vapor phase. The reactions are normally conducted at pressures of 101 kPa to 7000 kPa, and for vapor phase reaction are preferably at elevated pressures (e.g., between about 1460 kPa and 2190 kPa). The reaction is preferably conducted in the presence of activated carbon. Activated carbon is particularly advantageous for embodiments where the reaction is in the vapor phase.

By "activated carbon" is meant an amorphous carbon having high adsorptivity for gases, vapors and colloidal solids. Such activated carbons are typically formed from the carbon source by heating to about 800° C. to 900° C. with steam or carbon dioxide to confer upon the carbon a porous internal structure. Any of the well known activated carbons can be used in the practice of this invention as well as any carbons prepared by techniques known in the art to improve carbon adsorptivity. Commercially available activated carbons useful in the process of this invention include those sold under the following trademarks: Darco™, Nuchar™, Columbia SBV™, Columbia MBV™, Columbia MBQ™, Columbia JXC™, Columbia CXC™, Calgon PCB™, and Barnaby Cheny NB™. The carbon can be in the form of powder, granules, or pellets, etc. However, it is preferred to use granules to facilitate use in tubular reactors. The size of the granules is not critical but it is preferred to employ granules having an average mesh size of about ⅟25 to about ⅙ of the reactor diameter.

The process of this invention can be carried out readily using well known chemical engineering practice, which includes continuous, semi-continuous or batch operations. Lower temperatures, pressures and molar ratios of water to the carboxy and/or ether compounds, favor the formation of $CF_3CH=CF_2$ over $CF_3CH_2CF_3$. 1,1,1,3,3,3-Hexafluoropropane and 1,1,3,3,3-pentafluoropropene may be recovered from the reaction products by using conventional techniques such as decantation and/or distillation.

The reaction zone and its associated feed lines, effluent lines and associated units should be constructed of materials resistant to hydrogen fluoride. Typical materials of construction, well-known to the fluorination art, include stainless steels, in particular of the austenic type, the well-known high nickel alloys, such as Monel® nickel-copper alloys, Hastelloy® nickel-based alloys and Inconel® nickel-chromium alloys, and copper-clad steel. Also suitable for reactor fabrication are such polymeric plastics as polytrifluorochloroethylene and polytetrafluoroethylene, generally used as linings.

HFC-236fa is useful as a refrigerant, fire extinguishant, heat transfer medium, gaseous dielectric, sterilant carrier, polymerization medium, particulate removal fluid, carrier fluid, buffing and abrasive agent, displacement drying agent and power cycle working fluid. In particular, HFC-236fa is highly effective and as a refrigerant for use in refrigeration equipment.

HFC-1225zc is useful as a monomer for the preparation of fluoropolymers.

Practice of the invention will become further apparent from the following non-limiting examples.

EXAMPLE 1

$(CF_3)_2CHCO_2H+H_2O \rightarrow CF_3CH_2CF_3+CF_3CH=CF_2$

A mixture of 25 mL water, 50 mL acetone and 15.1 g (77 mmol) $(CF_3)_2CHCO_2H$ was heated in a stainless steel tube for 16 hours at 100° C. The reaction product was discharged from the reaction vessel and collected in a cold trap (−78° C.). A liquid (9 mL) was collected and based on $^{19}F$ and $^1H$ NMR was found to contain 20% acetone, 75% $CF_3CH_2CF_3$ and 5% $CF_3CH=CF_2$. The crude product was distilled through a low-temperature column and a mixture (9.4 g) containing 95% $CF_3CH_2CF_3$ and 5% $CF_3CH=CF_2$ was isolated. The conversion of $(CF_3)_2CHCO_2H$ was 85%.

EXAMPLE 2

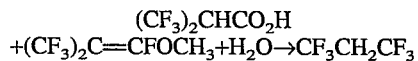
$(CF_3)_2CHCO_2H$
$+(CF_3)_2C=CFOCH_3+H_2O \rightarrow CF_3CH_2CF_3$ $(CF_3)_2CHCO_2H$ was dissolved in water (20 mL). The pH of this solution as measured by pH paper was less than 1. $(CF_3)_2C=CFOCH_3$ (10.1 g, 90% purity, the rest being $(CF_3)_2CHCF_2OCH_3$) was added to the above solution. The reaction solution was heated in a stainless steel tube for 14 hours at 180° C. under autogenous pressure. After cooling, the reaction product was discharged from the reaction vessel and collected in a cold trap (−78° C.). The product (5 mL, 6.9 g) was analyzed by $^{19}F$ NMR and found to contain $CF_3CH_2CF_3$ and $(CF_3)_2C=CFOCH_3$ in a ratio of 95:5, respectively. The conversion of $(CF_3)_2CHCO_2H$ was 100% and the conversion of $(CF_3)_2C=CFOCH_3$ was 70%. The isolated yield of $CF_3CH_2CF_3$ was 56%.

EXAMPLE 3

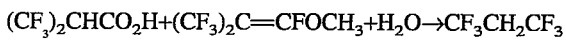
$(CF_3)_2CHCO_2H+(CF_3)_2C=CFOCH_3+H_2O \rightarrow CF_3CH_2CF_3$

A mixture of 50 mL water, 25 mL concentrated sulfuric acid, 2.0 g $(CF_3)_2CHCO_2H$ and 21.2 g $(CF_3)_2C=CFOCH_3$(ether B) is heated in a Hastelloy™ nickel alloy tube for 6 hours at 200° C. The volatile gases are sampled and include carbon dioxide and $CF_3CH_2CF_3$ (HFC-236fa).

EXAMPLE 4

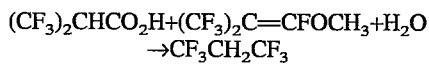
$(CF_3)_2CHCO_2H+(CF_3)_2C=CFOCH_3+H_2O$
$\rightarrow CF_3CH_2CF_3$

A mixture of 150 mL water, 3.9 g $(CF_3)_2CHCO_2H$ and 31.8 g $(CF_3)_2C=CFOCH_3$ (ether B) is heated in a Hastelloy™ nickel alloy tube for 6 hours at 200° C. The gases are bubbled through a solution of aqueous NaOH and a $CaSO_4$ drying column, and are condensed in a dry ice cooled trap. The product which is recovered includes $CF_3CH_2CF_3$ (HFC-236fa).

EXAMPLE 5

$(CF_3)_2CHCO_2H + (CF_3)_2C\!\!=\!\!CFOCH_3 + H_2O \rightarrow CF_3CH_2CF_3$

A mixture of 50 mL water, 1 mL concentrated sulfuric acid, 0.98 g $(CF_3)_2CHCO_2H$ and 10.0 g $(CF_3)_2C\!\!=\!\!CFOCH_3$ (ether B) is refluxed for 25 hr at 88°–90° C. The material which is recovered includes HFC-236fa, as well as starting ether B.

EXAMPLE 6

$(CF_3)_2CHCO_2H + (CF_3)_2C\!\!=\!\!CFOCH_3 + H_2O \rightarrow$
$CF_3CH_2CF_3$

A mixture of 50 g water, 0.98 g $(CF_3)_2CHCO_2H$ (2.8 g) and 15 g $(CF_3)_2C\!\!=\!\!CFOCH_3$ (ether B) is heated in a Hastelloy™ nickel alloy tube for 8 hours at 200° C. The product includes HFC-236fa.

EXAMPLE 7

$(CF_3)_2CHCO_2H + (CF_3)_2CHCF_2OCH_3 + H_2O \rightarrow$
$CF_3CH_2CF_3$

A 30 g mixture containing $(CF_3)_2CHCF_2OCH_3$ (ether A) $(CF_3)_2CHCO_2H$ (2.53 g) is heated in a Hastelloy™ nickel alloy tube with 50 mL water and 100 mL ethylene glycol dimethyl ether for 6 hours at 200° C. The product includes HFC-236fa.

EXAMPLE 8

$(CF_3)_2CHCO_2H + (CF_3)_2CHCF_2OCH_3 +$
$(CF_3)_2C\!\!=\!\!CFOCH_3 + H_2O \rightarrow CF_3CH_2CF_3$ A 100 g mixture containing 59% $(CF_3)_2CHCF_2OCH_3$ (ether A), 20% $(CF_3)_2C\!\!=\!\!CFOCH_3$ (ether B), 16% toluene, and 5% $(CF_3)_2CHCO_2H$ together with 50 mL water and 100 mL bis(2-methoxyethyl) ether is heated in a Hastelloy™ nickel alloy tube for 3 hours at 135° C. and 6 hours at 200° C. The product includes HFC-236fa.

EXAMPLE 9

$(CF_3)_2CHCO_2H + (CF_3)_2CHCF_2OCH_3 + H_2O \rightarrow$
$CF_3CH_2CF_3 + CF_3CH\!\!=\!\!CF_2$ Activated carbon (25 g, 1/8" (0.32 mm) diameter pellets) and deionized water (5 g) are loaded into a 1" (2.54 cm) OD×12" (30.5 cm) length Inconel™ 600 nickel alloy tube. The reactor temperature is raised to 320° C. and the reactor pressure adjusted to 230 psig (1690 kPa). $(CF_3)_2CHCF_2OCH_3$ (ether A, 9.2 g) and a solution of $(CF_3)_2CHCO_2H$ (2.0 g) in water (6 mL) are independently and continuously fed to the reactor over 3 hours. After the feed flow is stopped, the reactor is flushed with deionized water (10 g). The reactor effluent is scrubbed to remove HF. The product includes both HFC-236fa and $CF_3CH\!\!=\!\!CF_2$ (HFC-1225zc).

EXAMPLE 10

$(CF_3)_2CHCO_2H + (CF_3)_2CHCF_2OCH_3 + H_2O \rightarrow$
$CF_3CH_2CF_3 + CF_3CH\!\!=\!\!CF_2$ Activated carbon (25 g, 1/8" (0.32 mm) diameter pellets) and deionized water (5.8 g) are loaded into a 1" (2.54 cm) OD×12" (30.5 cm) length Inconel™ 600 nickel alloy tube. The reactor temperature is raised to 280° C. and the reactor pressure adjusted to 230 psig (1690 kPa). $(CF_3)_2CHCF_2OCH_3$ (ether A, 6.8 g) and a solution of $(CF_3)_2CHCO_2H$ (1.5 g) in water (10 mL) are independently and continuously fed to the reactor over 3 hours. After the feed flow is stopped, the reactor is flushed with deionized water (11.2 g). The reactor effluent is scrubbed to remove HF. The product includes HFC-236fa and $CF_3CH\!\!=\!\!CF_2$ (HFC-1225zc).

EXAMPLE 11

$(CF_3)_2CHCO_2H + (CF_3)_2CHCF_2OCH_3 + H_2O \rightarrow$
$CF_3CH_2CF_3 + CF_3CH\!\!=\!\!CF_2$ Activated carbon (25 g, 1/8" (0.32 mm) diameter pellets) and deionized water (10 g) are loaded into a 1" (2.54 cm) OD×12" (30.5 cm) length Inconel™ 600 nickel alloy tube. The reactor temperature is raised to 350° C. and the reactor pressure adjusted to 0 psig (101 kPa). $(CF_3)_2CHCF_2OCH_3$ (ether A, 53.4 g) and a solution of $(CF_3)_2CHCO_2H$ (4.5 g) in water (10 mL) are independently and continuously fed to the reactor over 5 hours. After the feed flow is stopped, the reactor is flushed with deionized water (10 g). The reactor effluent is scrubbed to remove HF. The product includes HFC-236fa and $CF_3CH\!\!=\!\!CF_2$ (HFC-1225zc).

EXAMPLE 12

$(CF_3)_2CHCO_2H + (CF_3)_2CHCF_2OCH_3 + H_2O \rightarrow$
$CF_3CH_2CF_3 + CF_3CH\!\!=\!\!CF_2$ Activated carbon (25 g, 1/8" (0.32 mm) diameter pellets) and deionized water (5.3 g) are loaded into a 1" (2.54 cm) OD×12" (30.5 cm) length Inconel™ 600 nickel alloy tube. The reactor temperature is raised to 250° C. and the reactor pressure adjusted to 150 psig (1140 kPa). $(CF_3)_2CHCF_2OCH_3$ (ether A, 21.1 g) and a solution of $(CF_3)_2CHCO_2H$ (1.8 g) in water (10 mL) are independently and continuously fed to the reactor over 5 hours. The reactor effluent is scrubbed to remove HF. The product includes HFC-236fa and $CF_3CH\!\!=\!\!CF_2$ (HFC-1225zc).

EXAMPLE 13

$(CF_3)_2CHCO_2H + (CF_3)_2CHCF_2OCH_3 + H_2O \rightarrow$
$CF_3CH_2CF_3 + CF_3CH\!\!=\!\!CF_2$ Activated carbon (25 g, 1/8" (0.32 mm) diameter pellets) and deionized water (20 g) are loaded into a 1" (2.54 cm) OD×12" (30.5 cm) length Inconel™ 600 nickel alloy tube. The reactor temperature is raised to 250° C. and the reactor pressure adjusted to 0 psig (101 kPa). $(CF_3)_2CHCF_2OCH_3$ (ether A, 21.5 g) and a solution of $(CF_3)_2CHCO_2H$ (1.8 g) in water (10 mL) and tetrahydrofuran (20 mL) are independently and continuously fed to the reactor over 5 hours. The reactor effluent is scrubbed to remove HF. The product includes HFC-236fa and $CF_3CH\!\!=\!\!CF_2$ (HFC-1225zc).

EXAMPLE 14

$(CF_3)_2CHCO_2H + (CF_3)_2CHCF_2OCH_3 + H_2O \rightarrow$
$CF_3CH_2CF_3 + CF_3CH\!\!=\!\!CF_2$ Activated carbon (25 g, 1/8" (0.32 mm) diameter pellets) and deionized water (24.4 g) are loaded into a 1" (2.54 cm) OD×12" (30.5 cm) length Inconel™ 600 nickel alloy tube. The reactor temperature is raised to 175° C. and the reactor pressure adjusted to 30 psig (310 kPa). $(CF_3)_2CHCF_2OCH_3$ (ether A, 21.0 g) and a solution of $(CF_3)_2CHCO_2H$ (1.8 g) in water (10 mL) are independently and continuously fed to the reactor over 5 hours. The reactor effluent is scrubbed to remove HF. The product includes HFC-236fa and $CF_3CH=CF_2$ (HFC-1225zc).

EXAMPLE 15

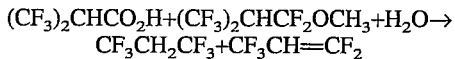

$(CF_3)_2CHCF_2OCH_3$ (ether A, 7.1 g) and a solution of $(CF_3)_2CHCO_2H$ (0.6 g) in water (10 mL) are independently and continuously fed to the reactor over 5 hours. The reactor is preheated to 450° C. and maintained at this temperature throughout the run. The reactor pressure is maintained at about atmospheric pressure. The reactor effluent is scrubbed to remove HF. The product includes $CF_3CH=CF_2$ (HFC-1225zc) and HFC-236fa.

Prophetic Examples 3 through 15 illustrate various embodiments of the process of the present invention, including the use of various temperature and pressure conditions. In general, the relative amount of $CF_3CH=CF_2$ in the product compared to $CF_3CH_2CF_3$ increases with increasing temperature and decreasing pressure.

What is claimed is:

1. A process for producing at least one compound selected from the group consisting of 1,1,1,3,3,3-hexafluoropropane and 1,1,1,3,3-pentafluoropropene, comprising:

(1) providing a mixture comprising water and at least one carboxy compound selected from the group consisting of $(CF_3)_2CHCO_2H$ and its water soluble salts, said mixture having a pH of less than about 4; and (2) reacting the mixture provided in (1) at an elevated temperature of at least about 75° C.

2. The process of claim 1 wherein the mixture provided in (1) further comprises at least one ether compound selected from the group consisting of compounds having the formula $(CF_3)_2CHCF_2OR$ and compounds having the formula $(CF_3)_2C=CFOR$, wherein R is an alkyl group of the formula $C_nH_{2n+1}$ and n is an integer from 1 to 6.

3. The process of claim 2 wherein the mixture is reacted in the presence of activated carbon.

4. The process of claim 3 wherein the mixture is reacted in the vapor phase.

5. The process of claim 2 where R is $CH_3$.

6. The process of claim 1 wherein the mixture provided in (1) is reacted to the liquid phase at a temperature of from about 150° to 250° C. to produce $CF_3CH_2CF_3$.

7. The process of claim 1 wherein the mixture provided in (1) is reacted in the vapor phase at a temperature of from about 150° C. to product $CF_3CH_2CF_3$.

8. The process of claim 1 wherein the carboxy compound is $(CF_3)_2CHCO_2H$; and wherein said $(CF_3)_2CHCO_2H$ is produced by reacting perfluoroisobutylene with water.

9. The process of claim 1 wherein the reaction of (2) is done in the presence of an inert organic material.

10. The process of claim 9 wherein said perfluoroisobutylene is reacted with a mixture of water and an alkanol of the formula ROH, wherein R is an alkyl group of the formula $C_nH_{2n+1}$ and n is an integer from $(CF_3)_2CHCO_2H$ and water to 6, to produce $(CF_3)_2CHCO_2H$ together with at least one ether compound selected from the group consisting of compounds of the formula $(CF_3)_2CHCF_2OR$ and compounds having the formula $(CF_3)_2C=CFOR$; and wherein said mixture of (1) comprises $(CF_3)_2CHCO_2H$ and said at least one ether compound and is reacted to produce $CF_3CH_2CF_3$.

11. The process of claim 10 wherein the reaction of said mixture is done in the presence of an inert organic material.

12. A process comprising: pyrolysis of chlorodifluoromethane to produce at least one of tetrafluoroethylene and hexafluoropropylene and by-product perfluoroisobutylene; reaction of said perfluoroisobutylene with water to form $(CF_3)_2CHCO_2H$; providing a mixture comprising said $(CF_3)_2CHCO_2H$ and water wherein the pH is less than about 4; and reacting said mixture at an elevated temperature of at least about 75° C. to produce at least one compound selected from the grup consisting of 1, 1, 1, 3, 3, 3-hexafluoropropane and 1, 1, 1, 3, 3-pentafluoropropene.

\* \* \* \* \*